United States Patent [19]

Maspero et al.

[11] Patent Number: 5,089,661
[45] Date of Patent: Feb. 18, 1992

[54] NEW PROCESS FOR THE PREPARATION OF 2-ARYL-PROPIONIC ACIDS

[75] Inventors: Federico Maspero, Milan; Oreste Piccolo, Como; Ugo Romano, Milan; Salvatore Gambino, Palermo, all of Italy

[73] Assignee: Enichem Synthesis S.p.A., Palermo, Italy

[21] Appl. No.: 580,363

[22] Filed: Sep. 10, 1990

Related U.S. Application Data

[63] Continuation of Ser. No. 180,580, Apr. 12, 1988, abandoned.

[30] Foreign Application Priority Data

Apr. 16, 1987 [IT] Italy .............................. 20149 A/87

[51] Int. Cl.$^5$ .............................................. C07C 63/04
[52] U.S. Cl. .................................. 562/493; 204/59 R; 562/440; 562/496; 562/479
[58] Field of Search ............. 204/59 R; 562/479, 490, 562/496, 493

[56] References Cited

U.S. PATENT DOCUMENTS

| 4,229,367 | 10/1980 | Granwehr et al. | 562/492 |
| 4,582,577 | 4/1986 | Wagenknecht | 204/59 R |
| 4,601,797 | 7/1986 | Wagenknecht | 204/59 R |
| 4,708,780 | 11/1987 | Silvestri et al. | 204/59 R |
| 4,814,494 | 3/1989 | Shimizu et al. | 562/465 |

OTHER PUBLICATIONS

Rieu et al, "Methods for the Synthesis of Antiinflammatory 2-Aryl Propionic Acids", *Tetrahedron*, vol. 42, No. 15, (1986), pp. 4095–4131.

*Primary Examiner*—John F. Niebling
*Assistant Examiner*—Steven P. Marquis
*Attorney, Agent, or Firm*—Birch, Stewart, Kolasch & Birch

[57] ABSTRACT

A new process is described for the preparation of a 2-aryl-propionic acid, such as for instance 2-[4-(2-methyl-propyl)phenyl]propionic or 2-(6'-methoxy-2'-naphthyl)propionic acid, through hydrogenation of a complex salt which consists of the mono- and/or di-valent anion of the corresponding 2-hydroxy-2-aryl-propionic acid, a di- or tri-valent metal cation, such as for instance Al(+3), Fe(+3), Zn(+2), or Mg(+2), and optionally other anonic or neutral ligands.

This new process is particularly advantageous in that the starting salt can be obtained directly via electrocarboxylation of the corresponding aryl methyl ketone, e.g. 4-(2-methyl-propyl)acetophenone or (6-methoxy-2-naphthyl) methyl ketone, with metal anodes which dissolve during the electrolysis.

17 Claims, No Drawings

NEW PROCESS FOR THE PREPARATION OF 2-ARYL-PROPIONIC ACIDS

This application is a continuation, of application Ser. No. 07/180,580 filed on Apr. 12, 1988, now abandoned.

The present invention relates to a new process for the preparation of 2-aryl-propionic acids of general formula (I)

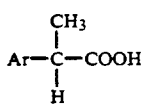

(I)

wherein
Ar represents an optionally substituted phenyl, naphthyl or heteroaryl radical, which comprises hydrogenating a complex salt of the corresponding 2-hydroxy-2-aryl-propionic acid of formula (II)

$$M_mX_xY_yL_l$$ (II)

wherein
M is a bi- or tri-valent metal cation
m is 1 or 2
X is a mono- or bi-valent anion of formula (III)

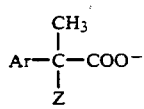

(III)

wherein
Z is —OH or —O⁻, or the corresponding hypercarboxylated form (IV)

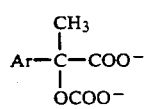

(IV)

wherein
Ar is as defined above
x is 1, 2, or 3,
Y is an organic mono- or di-valent anion,
y is 0 or an integer of from 1 to 4,
L is a neutral organic ligand,
l is 0 or a number comprised between 1 and 4, and the relationship between "m", "x", and "y" is such to provide for the electroneutrality of the salt, i.e. the product of "m" and the oxidation state of the metal "M" is equal to the sum of the product of "y" and the valence of the anion "Y", and the product of "x" and the valence of the anion "X". Non-steroidal antiinflammatory (NSAI) agents are one of the largest class of drugs both due to their high number and their therapeutic interest. Non-steroidal antiinflammatory agents can be classified according to their chemical structure into four main classes. The most thoroughly studied one is the class of 2-aryl-propionic acids, whose chemical structures fall within the above reported formula (I). As representatives of this class there may be cited the compound of formula (I) wherein Ar is 4-(2-methyl -propyl)phenyl, which is commonly indicated with the international non-proprietary name (INN) ibuprofen and is marketed under different trade-names, the most common being Brufen ®; the dextro isomer of the compound of formula (I) wherein Ar is a 6-methoxy-2-naphthyl radical which is known as naproxen and is marketed under different trade-marks including Naprosyn ®; the compound of formula (I) wherein Ar represents a 3-phenoxy-phenyl radical which is known as fenoprofen and marketed, as the corresponding calcium salt, as Feprona ®, Fenopron ®, or Nalfon ®; the compound wherein Ar is 2-fluoro-4-biphenylyl, known as flurbiprofen and marketed as Froben ®; the compound of formula (I) wherein Ar designates a 7-methoxy-10-methyl-phenothiazinyl radical (protizinic acid) marketed as Pirocrid ®; the compound of formula (I) wherein Ar is a 7-{5H-[1]benzopyran[2,3-b]pyridin}yl radical which is known as pranoprofen and marketed as Niflan ®, etc.

The importance of these compounds which actually represent the non-steroidal antiinflammatory drugs most widely and effectively used in the treatment of arthritis has increased to the point that a great number of different synthetic methods have been developed (see for instance the review published in Tetrahedron, Vol. 42, pp. 4095-4131 (1986), entitled "Methods for the synthesis of antiinflammatory 2-aryl -propionio acids").

Some of these methods involve 2-hydroxy-2-aryl-propionic acids of formula (V)

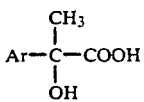

(V)

as intermediates.

These compounds are then converted into the desired aryl-propionic acids by hydrogenolysis directly or by dehydration followed by hydrogenation.

Methods for preparing the intermediates 2-hydroxy-2-aryl-propionic acids through electrochemical carboxylation of carbonyl compounds, have been reported recently in the patent and open literature.

In U.S. Pat. No. 4,601,797, as well as in Japanese patent applications J6 0100536 (Chem.Abs. 103, 214989y) and J6 0103193 (Chem.Abs. 103, 131247d) and, more particularly, in EP-A-189120, preparation of these 2-hydroxy-2-aryl-propionic acids (whose only interest as intermediates in the synthesis of the desired 2-aryl-propionic acids is acknowledged), is described through electrocarboxylation of the corresponding aryl methyl ketones. When, according to the process described in EP-A-189,120 and to a preferred embodiment of the process described in U.S. Pat. No. 4,601,797, the electrocarboxylation reaction is carried out with a metal anode which dissolves, as a metal cation, during the electrocarboxylation reaction (dissolving anodes), a complex salt of the desired 2-hydroxy-2-aryl-propionic acid with the anode metal cation is obtained. The salt which forms is then recovered from the reaction medium and hydrolysed by treatment with an acidic aqueous solution to the intermediate free 2-hydroxy-2-aryl-propionic acid of formula (V). This last compound is then converted into the desired 2-aryl-propionic acid, as anticipated, either by hydrogenolysis or by dehydration followed by hydrogenation.

It has now surprisingly been found that it is possible to obtain the desired 2-aryl-propionic acid, by directly hydrogenating the complex salt of the 2-hydroxy-2-aryl-propionic acid, with no need to hydrolyse this salt to the free acid form, as provided for by the processes of the above cited patents and patent applications.

The advantages in the industrial practice due to the possibility of avoiding a whole step (the hydrolysis of the salt to give the free 2-hydroxy-acid), are apparent.

Besides the indirect economical advantages obviously deriving from this remarkable simplification of the preparation process, as a direct result, the yields obtained in the hydrogenation of salt (II) are almost quantitative and the obtained product is of a purity greater than that obtainable with the prior-art processes which run through the free hydroxy-acid. For the purposes of the present invention, the term "optionally substituted phenyl or naphthyl radical", used in defining Ar, designates a phenyl or naphthyl radical which may be unsubstituted or substituted with one to three substituents, which are the same or different, and do not negatively interfere with the electrocarboxylation and hydrogenation reactions. In particular, substituents which may be present, are, for instance, alkyl, phenyl, alkoxy, phenoxy, fluoro and chloro.

The term "optionally substituted heteroaryl radical" represents a mono- or poly-cyclic heteroaromatic radical which may contain from 1 to 3 heteroatoms independently selected from oxygen, nitrogen and sulfur, and be unsubstituted or bear one or more substituents, which are the same or different, as defined above.

According to a preferred embodiment of the present invention, Ar is selected from the group consisting of 4-(2-methyl-propyl)phenyl, 3-phenoxy-phenyl, 2-fluoro-4-biphenylyl, 7-methoxy-10-methyl-2-phenothiazinyl, and 6-methoxy-2-naphthyl. The acids of formula (I) wherein Ar has the above meanings are in fact the most interesting NSAI compounds.

According to a most preferred embodiment of the present invention Ar is 4-(2-methyl-propyl)phenyl or 6-methoxy-2-naphthyl.

The term "bi- or tri-valent metal cation" refers t any metal cation with (II) or (III) oxidation state, such as for instance, a bi-valent alkaline earth metal cation, and in particular Mg, a tri-valent Group III metal cation, in particular Al, or a bi- or tri-valent cation of the first transition elements, in particular Fe, Cu, and Zn.

The term "mono- or bi-valent organic anion" includes hydroxyl ion, $(C_1-C_8)$alcoholate, such as methylate, isopropylate, 1-phenyl-ethylate, etc., carbonate and carboxylate deriving from aliphatic mono- or bi-carboxylic acids such as acetate, propionate, oxalate, etc.

Finally, the term "neutral organic ligand" designates any organic molecule with zero ionic charge, which contains at least one atom with a lone ion pair, such as for instance an alkanol, e.g. methanol, and ethanol, a linear or cyclic ether, e.g. diethyl ether, tetrahydrofuran, and dioxane, an amide, e.g. dimethylformamide, and acetamide, a nitrile, e.g. acetonitrile, and propionitrile, a sulfoxide, e.g. dimethylsulfoxide, etc.

The 2-hydroxy-2-aryl-propionic acid complex metal salt which is hydrogenated, according to the present invention to afford the desired 2-aryl-propionic acid, is here indicated by the structure reported in general formula (II).

The meanings of y, Y, l, and L in formula (II) will generally depend on the process used for preparing the complex salt. As an example, when the complex salt is prepared starting from a compound of formula $M_m$, $Y_y$, and the 2-hydroxy-2-aryl-propionic acid of formula (V), the complex salt will probably contain the anion Y, and the value of y will depend on the molar ratio among the reaction partners. The use of a particular solvent as the reaction medium or to precipitate the complex salt, might lead to the inclusion of one or more solvent neutral molecules as L ligands.

Finally, when, according to a preferred embodiment of the present invention, the complex salt is obtained via electrocarboxylation of the corresponding aryl methyl ketone, it might also contain oxalate and/or carbonate ions, deriving from the electrochemical carboxylation reaction, neutral solvent molecules, and both structures (III) and (IV) for X.

Hydrogenation of the complex salt of formula (II) according to the present invention, is a reaction of a general applicability, independently on the process used for preparing the starting compound; it is however industrially convenient when the starting complex salt is obtained by a process which does not involve passing through the free 2-hydroxy-2-aryl-propionic acid, e.g. when the starting salt is obtained by electrochemical carboxylation of the corresponding aryl methyl ketone with dissolving anodes.

It is therefore a further object of the present invention a process for preparing a 2-aryl-propionic acid of formula (I) wherein Ar is as defined above, which comprises submitting to electrocarboxylation the corresponding aryl methyl ketone of formula (VI)

in a diaphragm-less cell with dissolving metal anodes, recovering the thus formed 2-hydroxy-2-aryl-propionic acid complex salt and hydrogenating it. Anode materials which may conveniently be employed in the electrolysis of the aryl methyl ketones of formula (VI), are, for instance, aluminum, zinc, iron, copper, magnesium, optionally alloyed with each other, and, more generally, those metals which, in the electrolysis reaction medium, have an anodic dissolution voltage lower than that of the other species present in solution.

According to a preferred embodiment of the present invention M therefore represents a bi- or tri-valent metal cation selected from the group substantially consisting of Al, Fe, Cu, Zn, and Mg.

According to a most preferred embodiment of the present invention, in view of the optimum results which are obtained in the electrocarboxylation of aryl methyl ketones with aluminum anodes, as reported in EP-A-189,120, M represents a tri-valent aluminum cation.

Hydrogenation of the salt of formula (II) according to the present invention, may be carried out either in the presence or in the absence of molecular hydrogen under homogeneous or heterogeneous catalysis conditions. More particularly, the reaction can be conducted in a stream of hydrogen or under hydrogen atmosphere at a pressure which may be equal to or higher than the atmospheric pressure, optionally in the presence of an inert gas, such as nitrogen, or argon, or otherwise hydrogen can be generated in situ by suitable hydrogen donors, wherein "hydrogen donor" designates any organic substance that in the presence of a suitable catalyst, spontaneously oxidises itself releasing hydrogen.

In the former case, the reaction may be carried out at hydrogen pressures comprised between 1 and 100 atmospheres, and, preferably, between 5 and 50 atmospheres.

In the latter case, "hydrogen donors" which could suitably be employed are, for instance, hydrazine, secondary alcohols, e.g. isopropyl alcohol, sec-butyl alcohol, 1-phenyl-ethyl alcohol, etc., olefins, e.g. 1-hexene, cyclohexene, etc.

Suitable catalysts for the hydrogenation of the complex salts of formula (II), according to the present invention are, for instance, the Group VIII elements and typically finely divided palladium and platinum, optionally supported on inert materials such as carbon and asbestos, rhodium, iridium, platinum and ruthenium complexes optionally modified with ligands such as phosphines, arsines, tertiary nitrogen bases, etc., nickel-Raney or pure nickel, and the like catalysts commonly used in hydrogenation reactions.

Said catalysts are employed in amounts sufficient to provide quantitative hydrogenation yields with an industrially acceptable reaction rate. Generally, when the reaction is carried out under heterogeneous catalysis conditions, an amount of catalyst comprised between 0.5 and 20% by weight, calculated on the weight of the starting substrate, and preferably comprised between 5 and 15%, is employed. When the reaction is carried out under homogeneous catalysis conditions, a smaller amount of catalyst will be used, generally comprised between 0.1 and 10% by weight, calculated on the weight of the substrate to be hydrogenated, and preferably comprised between 0.5 and 5%. For economic reasons it is however desirable to use the smallest possible amount of catalyst, which can be determined very easily by any skilled technician by means of simple tests.

Generally, the optimum temperature for the reaction depends on the particular type of catalyst employed. Preferably, however, the reaction is conducted at a temperature higher than room temperature and typically comprised between 50° and 180° C. The reaction is carried out in the presence of an organic solvent or a suitable mixture of organic solvents, which is capable of dissolving the starting salt of formula (II), is stable under the hydrogenation conditions and is compatible with the particular catalyst employed in the hydrogenation reaction.

Suitable solvents are for instance lower aliphatic alcohols, e.g. methanol, ethanol, etc., ethers and polyethers, e.g. dioxane, bis-(2-methoxyethyl) ether, dimethoxyethane, etc., aliphatic carboxylic acids and the alkyl esters thereof, e.g. acetic acid, ethyl acetate, propionic acid, and methyl propionate, aliphatic nitriles, e.g. acetonitrile, propionitrile, etc., halogenated hydrocarbons, such as methylene chloride, dichlorethane, chloroform, etc., amide-like solvents, e.g. dimethylformamide, and dimethylacetamide, and dimethylsulfoxide.

In some instances it is also possible to use the "hydrogen-donor" as the reaction solvent, e.g. when the "hydrogen donor" is isopropanol, or 1-phenyl-ethanol. In this case the alcohol will behave both as the solvent and the "hydrogen donor" and hydrogenation will be easily carried out by adding the catalyst to a solution of the salt of formula (II) in e.g. isopropanol or 1-phenylethanol.

At the end of the reaction, which will typically be complete in a few hours, in the case of heterogeneous catalysis, the heterogeneous catalyst is filtered off and the solvent is removed. The thus obtained residue may then be purified according to conventional techniques which involve, for instance, dissolving the residue in aqueous alkaline solution, washing the obtained solution with water-immiscible organic solvents and precipitating the desired acid of formula (I) by acidification with mineral acids. In the case of homogeneous catalysis, the procedure for recovering the desired product will depend on the particular type of catalyst employed. Generally, however, once the solvent has been removed, it is possible, to follow substantially the same purification procedure outlined in the case of heterogeneous catalysis, if, as usually occurs, the catalyst is removed by washing with the water-immiscible solvent. If desired, the thus obtained 2-aryl-propionic acid can be further purified and/or resolved into the single isomers, according to the conventional methods known in literature.

When, according to a preferred embodiment of the present invention, the salt of formula (II) is obtained via electrochemical carboxylation in a diaphragm-less cell with dissolving anodes, according to the teachings of EP-A-189,120 and U.S. Pat. No. 4,601,797, which are incorporated herein by reference, the salt is selectively precipitated from the reaction mixture by the addition of a precipitating solvent or a mixture of precipitating solvents.

Said precipitating solvents are selected from those classed as apolar or slightly polar organic solvents which do not precipitate the starting aryl methyl ketone and, preferably, from the slightly polar organic solvents which do not precipitate the supporting electrolyte used in the electrocarboxylation step. Suitable solvents are, for instance, aliphatic ethers, lower aliphatic alcohols, halogenated aliphatic or aromatic hydrocarbons, ketones, etc. Preferably, said precipitating solvents will be selected from the group consisting of aliphatic ethers and alcohols and halogenated hydrocarbons and more preferably from the ethers such as methyl tert-butyl ether or methyl isopropyl ether.

These solvents in fact besides selectively precipitating the salt of formula (II), are also particularly advantageous as far as recycling of the electrolytic solution is concerned. Owing in fact to their low boiling points, they can be easily removed from the filtrate by simple evaporation thus allowing an easy recycle thereof. Furthermore it has been demonstrated that these solvents do not interfere with the electro carboxylation reaction when they are present in the recycling solution in amounts which are insufficient to precipitate the salt (II).

The precipitated salt of formula (II) is then washed with the precipitating solvent, dried, redissolved in the suitable solvent and hydrogenated under the above described conditions. As anticipated, the precipitate which is obtained from the electrocarboxylation reaction substantially consists of a compound of chemical structure (II).

The following examples which illustrate in detail the process of the present invention in some representative embodiments, are not to be construed as a limitation to the scopes of the invention itself.

EXAMPLE 1

A solution of 6-methoxy-2-acetonaphthone (20 g, 0.1 mol) and tetrabutylammonium bromide (3.7 g, 0.012 mol) in anhydrous dimethylformamide (100 ml) is electrolysed in a glass diaphragm-less cell, with aluminum electrodes (both anode and cathode). The electrocarboxylation reaction is carried out at a temperature of 10° C., under 2.5 atm. of $CO_2$.

The intensity of the current circulating through the cell is kept constant at 650 mA, gradually increasing cell potential from 3 to 7 V.

After about 6 hours, when chromatographic analysis shows a $\geq 90\%$ conversion of the starting ketone, the cell is emptied, the temperature is allowed to raise to room temperature and methyl alcohol (5 ml) and methyl tert-butyl ether (MTBE) (400 ml) are added to the reaction mixture. The obtained precipitate is recovered by filtration and washed with small amounts of MTBE affording an aluminum complex salt (32 g) with the following chemico-physical characteristics N.M.R. $\delta$[(multiplicity, relative intensity) in acetic acid $d_4 - TMS: \delta = 0$]

1.9 (s, 22)(3H, CH3); 2.4 (s, 3)(3H, CH$_3$); 2.9 (s, 36)(3H, DMF CH ); 3.0 (s, 36)(3H, DMF CH$_3$); 3.4 (s, 17)(3H, CH$_3$OH); 3.8 (s, 3)(3H, OCH$_3$); 3.9 (s, 24)(3H, OCH$_3$); 7.1÷7.2 (m, 20)(2 aromatic H); 7.6÷7.8 (m, 30)(3 aromatic H); 7.9÷8.1 (m, 22)(1 aromatic H+1 DMF formyl H).

I.R. (nujol) : 3450 (br), 2870 (s), 1680 (s), 1675 (s), 1620 (s), 1515 (m), 1495 (m), 1350 (w), 1280 (s), 1240 (m), 1210 (s), 1180 (m), 1150 (w), 1130 (w), 1110 (w), 1080 (m), 1040 (s), 980 (w), 940 (w), 910 (s), 870 (m), 850 (m), 825 (w), 785 (w), 770 (w), 735 (m), 600 (br), 495 (m) cm$^{-1}$.

Elemental analysis : Al 5.7%; C 53.8%; H 6.0%; N 3.7% This product is dissolved in acetic acid (100 ml), 5% Pd/C (4 g) is then added to the thus obtained solution, and the hydrogenation reaction is conducted at 120° C. under a hydrogen pressure of 20 atmospheres. After 4 hours the reaction is complete. The catalyst is then removed by filtration, the solvent is evaporated off to dryness and the residue is dissolved in a two-phase system consisting of 10% aqueous NaOH (100 ml) and toluene (20 ml).

The aqueous alkaline phase is then separated and brought to pH 3 by the addition of concentrated HCl. The solid which precipitates and is recovered by filtration (19 g) consists of raw aluminum-free (R,S)2-(6'-methoxy-2'-naphthyl)propionic acid, with a minimum titre greater than 95%.

EXAMPLE 2

By following substantially the same procedure as in the foregoing example but starting from 4-(2-methyl-propyl)acetophenone (10 g) instead of 6-methoxy-acetonaphthone and using a slightly lower amount of tetrabutyl ammonium bromide (3.5 g), (R,S)2-(4-(2-methyl-propyl)phenyl)propionic acid (11.5 g) is obtained with a titer of 96%.

EXAMPLE 3

The process of example 1 has been repeated by using a zinc anode instead of an aluminum anode.

The intermediate zinc salt has been hydrogenated under the conditions of example 1 affording the desired (R,S)2-(6'-methoxy-2'-naphthyl)propionic acid (with a titre greater than 95%) with an 81% yield calculated on the starting ketone (18.6 g).

EXAMPLES 4-6

The procedure of example 1 has been substantially repeated by varying the solvent used for precipitating the salt at the end of the electrocarboxylation step. The results are reported in following Table I wherein the solvents used instead of methyl alcohol (5 ml) and MTBE (400 ml), and the amount thereof, are indicated :

TABLE I

| Ex. no. | Precipitating solvent | % Yield |
|---|---|---|
| 4 | sec-butyl alcohol (350 ml) | 83 |
| 5 | methyl isobutyl ketone (400 ml) | 78 |
| 6 | methyl tert-butyl ether (400 ml) | 85 |

EXAMPLE 7

The hydrogenation reaction described in the second part of example 1 is repeated varying the hydrogenation conditions, and more particularly, using nickel-Raney (5 g) instead of Pd/C, and carrying out the hydrogenation at 140° C.

The desired product is obtained in 94% yield, calculated on the starting salt.

EXAMPLE 8

A solution of 6-methoxy-2-acetonaphthone (15.5 g, 77.5 mmol) and tetrabutyl ammonium bromide (3.6 g, 11.7 mmol) in anhydrous dimethylformamide (90 ml) is electrolysed in a diaphragm-less glass cell, under vigorous stirring, with aluminum electrodes (both cathode and anode). The electrocarboxylation reaction is carried out at a temperature of 10° C., under a $CO_2$ pressure of 2.5 atmospheres. The electrolysis is run at 650 mA constant current, gradually increasing cell potential from 3 to 7 V.

After about 6 hours, when chromatographic analysis shows a $\geq 90\%$ conversion of the starting ketone, the cell is emptied, the temperature is allowed to raise to room temperature and methyl alcohol (5 ml) and methyl tert-butyl ether (MTBE) (300 ml) are added to the reaction mixture.

The precipitate which is obtained is recovered by filtration, washed with MTBE (100 ml) and dried under vacuum at 50° C. This precipitate (25 g) is dissolved in a mixture of acetic acid (25 ml) and dichloroethane (50 ml), RhCl(PPh$_3$)$_3$ (0.2 g) is added to the obtained solution and hydrogenation is conducted at 120° C. and a hydrogen pressure of 20 atmospheres. After 3 hours the reaction is complete. The solvent is then removed by under vacuum evaporation and the product is purified by following substantially the same procedure as in example 1, thus recovering 14.5 g of raw, aluminum-free (R,S)2-(6'-methoxy-2'-naphthyl)propionic acid, with a titre higher than 95%.

EXAMPLE 9

The aluminum salt of 2-hydroxy-2-(6'-methoxy-2'-naphthyl)propionic acid is prepared starting from the corresponding acid (10.0 g, 40.65 mmol) by treatment with aluminum isopropylate (5.53 g, 27.10 mmol) in refluxing toluene (100 ml), for 3 hours, gradually removing the isopropyl alcohol which forms by azeotropic distillation in a Dean-Stark apparatus. The reaction mixture is then cooled and the precipitated salt is recovered by filtration (10.2 g), dissolved in acetic acid (100 ml) and hydrogenated under the same conditions as in the second part of example 1.

(R,S)2-(6'-methoxy-2-naphthyl)propionic acid (8.45 g -90%) is obtained with a 97% titer.

EXAMPLE 10

Hydrogenation of the free acid

The aluminum complex salt (25 g) obtained by following the electrocarboxylation procedure described in the first part of example 1, is dissolved by triturating it with methyl isobutyl ketone (100 ml), water (200 ml) and concentrated HCl (20 ml). The organic phase is separated and extracted with 10% aqueous NaOH (200 ml). The free acid is precipitated from this aqueous alkaline solution, by acidification with concentrated HCl. The precipitate, which is separated by filtration, is washed with water and dried (10.0 g), and then suspended in glacial acetic acid (100 ml) and hydrogenated according to the procedure described in the second part of example 1. A tarry product (2.90 g) is thus obtained with a naproxen titer of 75%.

We claim:

1. A process for preparing an aryl-propionic acid of general formula (I)

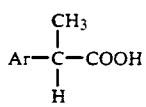

wherein

Ar designates an optionally substituted phenyl, naphthyl, or heteroaryl radical, which comprises a single step reaction of catalytically hydrogenating a complex salt of the corresponding 2-hydroxy-2-aryl-propionic acid of formula (II)

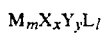

wherein

M is a bi- or tri-valent metal cation, m is 1 or 2

X is a mono- or di-valent anion of formula (III)

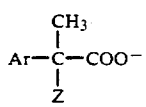

wherein

Z is —OH or —O, and

Ar is as defined above, or the corresponding hypercarboxylated form of formula (IV)

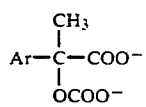

wherein

Ar is defined above

X is 1, 2, or 3

Y is a mono- or di-valent organic anion, y is 0 or an integer comprised between 1 and 4, L is a neutral organic ligand, l is 0 or a number between 1 and 4, and the relationship between "m", "x", and "y" are such to provide for salt electroneutrality.

2. The process of claim 1 wherein Ar is selected from 4-(2-methyl-propyl)phenyl, 3-phenoxy-phenyl 2-fluoro-biphenylyl, 7-methoxy-10-methyl-2-pheno thiazinyl, and 6-methoxy-2-naphthyl.

3. The process of claim 2 wherein Ar is selected from 4-(2-methyl-propyl)phenyl and 6-methoxy-2-naphthyl.

4. The process of claim 3 wherein Ar is 6-methoxy-2-naphthyl.

5. The process of claim 1 wherein M is selected from Al, Fe, Zn, Mg, and Cu.

6. The process of claim 5 wherein M is selected from $Al^{+3}$ and $Zn^{+2}$.

7. The process of claim 1 wherein the catalyst is selected from the group consisting of finely divided, optionally supported, palladium and platinum, rhodium, iridum, platinum, and ruthenium complexes optionally modified with ligands, nickel-Raney and pure nickel.

8. The process of claim 7 wherein the catalyst is palladium on carbon.

9. The process of claim 1 wherein hydrogen is generated in situ from a "hydrogen donor".

10. The process of any of claims 1 to 9 wherein the metal salt which undergoes hydrogenation is obtained via electrochemical carboxylation of the corresponding aryl methyl ketone in a diaphragm-less cell with a dissolving anode.

11. A process for the preparation of a 2-aryl-propionic acid of formula (I)

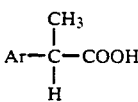

wherein

Ar designates an optionally substituted phenyl, napthyl, or heteroaryl radical, which comprises submitting to electrochemical carboxylation the corresponding aryl methyl ketone of formula (VI)

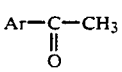

wherein

Ar is as defined above, in a diaphragm-less cell, with a dissolving anode, separating the thus formed metal complex salt and in a single step reaction catalytically hydrogenating said metal complex salt to provide said 2-aryl-propionic acid.

12. The process of claim 11 wherein Ar is selected from 4-(2-methyl-propyl)phenyl and 6-methoxy-2-naphthyl.

13. The process of claim 12 wherein Ar is 6-methoxy-2-napthyl.

14. The process of claim 11 wherein the metal salt is separated from the mixture deriving from the electrocarboxylation by precipitation with one or more precipitating solvents.

15. The process of claim 14 wherein the precipitating solvent is an ether.

16. The process of claim 15 wherein the precipitating solvent is methyl tert-butyl ether.

17. The process of claim 11 wherein the dissolving anodes employed in the electrocarboxylation step are formed from aluminum, zinc, magnesium, copper, iron and their alloys.

* * * * *